(12) United States Patent
Graziani et al.

(10) Patent No.: US 9,846,206 B2
(45) Date of Patent: Dec. 19, 2017

(54) SYSTEMS AND METHODS FOR MAGNETIC MATERIAL IMAGING

(71) Applicant: General Electric Company, Schenectady, NY (US)

(72) Inventors: Dominic Michael Graziani, Niskayuna, NY (US); Thomas Kwok-Fah Foo, Niskayuna, NY (US); Luca Marinelli, Schenectady, NY (US); Daniel Eugene Meyer, Niskayuna, NY (US); Bruce Allan Hay, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 1150 days.

(21) Appl. No.: 13/970,339

(22) Filed: Aug. 19, 2013

(65) Prior Publication Data

US 2014/0159712 A1 Jun. 12, 2014

Related U.S. Application Data

(60) Provisional application No. 61/735,396, filed on Dec. 10, 2012.

(51) Int. Cl.
*G01N 27/72* (2006.01)
*A61B 5/00* (2006.01)
(Continued)

(52) U.S. Cl.
CPC ........ *G01R 33/1276* (2013.01); *A61B 5/0515* (2013.01); *A61B 5/00* (2013.01)

(58) Field of Classification Search
CPC .......................... A61B 5/0515; G01R 33/1276
See application file for complete search history.

(56) References Cited

U.S. PATENT DOCUMENTS

| 2004/0097803 A1 | 5/2004 | Panescu |
| 2006/0238194 A1* | 10/2006 | Gleich ..................... A61B 5/05 324/309 |

(Continued)

FOREIGN PATENT DOCUMENTS

| WO | 2008060589 A2 | 5/2008 |
| WO | 2012098551 A1 | 7/2012 |

OTHER PUBLICATIONS

Merdes, "Locating a catheter transducer in a three-dimensional ultrasound imaging field", IEEE Trans Biomed Eng, vol. 48, Issue 12, pp. 1444-1452, Dec. 2001.

(Continued)

*Primary Examiner* — Serkan Akar
(74) *Attorney, Agent, or Firm* — Pabitra K. Chakrabarti (57) ABSTRACT

Magnetic material imaging (MMI) system including first and second sets of field-generating coils. Each of the field-generating coils of the first and second sets has an elongated segment that extends along an imaging axis of the medical imaging system. The imaging axis extends through a region-of-interest (ROI) of an object. The elongated segments of the first set of field-generating coils are positioned opposite the elongated segments of the second set of field-generating coils and the ROI is located between the first and second sets of field-generating coils. The MMI system also includes a coil-control module configured to control a flow of current through the first and second sets of field-generating coils to generate a selection field and to generate a drive field. The selection and drive fields combine to form a movable 1D field free region (FFR) that extends through the ROI.

12 Claims, 5 Drawing Sheets

(51) Int. Cl.
*G01R 33/12* (2006.01)
*A61B 5/05* (2006.01)

(56) References Cited

U.S. PATENT DOCUMENTS

| | | | |
|---|---|---|---|
| 2010/0063385 A1 | 3/2010 | Garibaldi et al. | |
| 2010/0168553 A1 | 7/2010 | Martel et al. | |
| 2011/0089942 A1* | 4/2011 | Goodwill | A61B 5/05 324/301 |
| 2011/0230758 A1 | 9/2011 | Eichler | |
| 2011/0237928 A1 | 9/2011 | Rahmer et al. | |
| 2011/0246103 A1 | 10/2011 | Rahmer et al. | |
| 2011/0295108 A1 | 12/2011 | Cox et al. | |
| 2012/0157823 A1 | 6/2012 | Gleich | |
| 2012/0310076 A1* | 12/2012 | Buzug | A61B 5/0515 600/409 |
| 2013/0241548 A1* | 9/2013 | Gleich | A61B 5/0515 324/307 |

OTHER PUBLICATIONS

Gleich et al., "Tomographic imaging using the nonlinear response of magnetic particles", Nature 435, pp. 1214-1217, Jun. 30, 2005.

Lederman, "Cardiovascular Interventional MRI", Circulation, vol. 112, Issue 19, pp. 3009-3017, Nov. 8, 2005.

Weizenecker et al., "Magnetic particle imaging using a field free line", Journal of Physics D: Applied Physics, vol. 41, Issue 10, 2008.

Goodwill at al., "Narrowband magnetic particle imaging", IEEE Trans Med Imaging, vol. 28, Issue 8, pp. 1231-1237, Aug. 2009.

Loke et al., "Magnetic Tracking System for Radiation Therapy", IEEE Transactions on Biomedical Circuits and Systems, vol. 4, Issue 4, pp. 223-231, Aug. 2010.

Rahmer et al., "Rapid 3D in vivo Magnetic Particle Imaging with a Large Field of View", 19th Annual Meeting International Society for Magnetic Resonance in Medicine, pp. 3285, 2011.

Goodwill et al., "Multidimensional x-space magnetic particle imaging", IEEE Trans Med Imaging, vol. 30, Issue 9, pp. 1581-1590, Sep. 2011.

Konkle et al., "Experimental 3D X-Space Magnetic Particle Imaging Using Projection Reconstruction", Magnetic Particle Imaging Springer Proceedings in Physics, vol. 140, pp. 243-247, 2012.

Haegele et al., "Visualization of Instruments for Cardiovascular Intervention Using MPI", Magnetic Particle Imaging Springer Proceedings in Physics, vol. 140, pp. 211-215, 2012.

Wojtczyk et al., "Visualization of Instruments in interventional Magnetic Particle Imaging (iMPI): A Simulation Study on SPIO Labelings", Magnetic Particle Imaging Springer Proceedings in Physics, vol. 140, pp. 167-172, 2012.

Goodwill et al., "Projection X-Space Magnetic Particle Imaging", IEEE Transactions on Medical Imaging, vol. 31, No. 5, May 2012.

Vogel et al., "Slicing Frequency Mixed Traveling Wave for 3D Magnetic Particle Imaging", Magnetic Particle Imaging, SPPHY 140, pp. 231-235.

* cited by examiner

SYSTEMS AND METHODS FOR MAGNETIC MATERIAL IMAGING

CROSS-REFERENCE TO RELATED APPLICATION

The present application claims the benefit of U.S. Provisional Application No. 61/735,396, filed on Dec. 10, 2012, which is incorporated by reference in its entirety.

BACKGROUND

The subject matter herein relates generally to medical imaging and, in particular, to systems and methods for magnetic material imaging.

In some medical procedures, surgical instruments may be tracked by imaging the position of the instrument in real-time with respect to the surrounding anatomy. For example, in one conventional method, a position of a catheter is continuously monitored by two-dimensional (2D) x-ray fluoroscopy and the surrounding tissue (e.g., vasculature) is visualized with contrast agent injections. Because of the continuous x-ray imaging, however, the total dose of ionizing radiation received by the patient during this procedure is a concern. In addition, nearby personnel are required to wear lead aprons to limit exposure to the ionizing radiation.

Other imaging modalities have been proposed for tracking surgical instruments, but these imaging modalities have certain problems or drawbacks such as high cost of equipment and/or operation, long acquisition times, substantial hardware or equipment modifications, or poor quality of images. For example, magnet resonance imaging (MRI) has been used to track surgical instruments. Generally, MRI can provide high resolution 3D images with excellent contrast of the surrounding anatomy. However, surgical tracking using MRI can be expensive, may have a low acquisition rate, and provides limited access to the patient compared to X-ray fluoroscopy. Moreover, any surgical instrument used in the procedure must be non-ferrous, potentially limiting the instruments available to the surgeon.

Ultrasound is another non-invasive imaging technology that has been applied to catheter tracking. One challenge with ultrasound tracking is that the catheter operates as a specular reflector. Therefore, it is often necessary modify the catheter in some way, such as placing a transducer on the tip, in order to visualize the catheter position in ultrasound. This can add to the bulk and cost of the instrument.

Accordingly, systems and methods for tracking surgical instruments without using imaging modalities that can be harmful to the patient or require costly equipment are generally desired. Magnetic particle imaging (MPI) is a recently developed imaging modality in which a spatial distribution of magnetic particles can be determined. For example, MPI is capable of imaging a distribution of superparamagnetic iron oxide particles (SPIOs) with a relatively high sensitivity, high spatial resolution and high imaging speed. In particular, MPI detects the magnetization change caused when a sensitive region passes through the sample (e.g., a region in which there is little or no magnetic field surrounded by a larger saturating field). Unlike other imaging modalities, MPI is free of ionizing radiation. The known systems are directed to imaging a single point and moving that point relative to the object-of-interest. With a sensitive point configuration, image acquisition is inherently three dimensional which can therefore result in significantly long acquisition times.

BRIEF DESCRIPTION

In one embodiment, a magnetic material imaging (MMI) system is provided that includes first and second sets of field-generating coils. Each of the field-generating coils of the first and second sets has an elongated segment that extends along an imaging axis of the medical imaging system. The imaging axis extends through a region-of-interest (ROI) of an object. The elongated segments of the first set of field-generating coils are positioned opposite the elongated segments of the second set of field-generating coils and the ROI is located between the first and second sets of field-generating coils. The MMI system also includes a coil-control module configured to control a flow of current through the first and second sets of field-generating coils to generate a selection field and to generate a drive field. The selection and drive fields combine to form a movable 1D field free region (FFR) that extends through the ROI. The MMI system also includes a detection assembly that is positioned relative to the ROI to detect changes in magnetization of magnetic material located proximate to the 1D FFR in the ROI.

In another embodiment, a magnetic material imaging (MMI) system is provided that includes first and second field units that are spaced apart from each other. Each of the first and second field units includes field-generating coils that have corresponding elongated segments. The elongated segments of the first and second field units extend generally along one another. The MMI system also includes a coil-control module that is configured to control a flow of current through the field-generating coils to generate a 1D free field region (FFR) between the first and second field units. The MMI system also includes a detection assembly that is positioned relative to the object to detect changes in magnetization of magnetic material located proximate to the 1D FFR. The MMI system also includes a positioning system that has first and second arms that are coupled to and support the first and second field units, respectively. The positioning system is configured to move (e.g., rotate, shift) the first and second field units to move an imaging volume with respect to the object/patient.

In yet another embodiment, a method of imaging a region-of-interest (ROI) in a patient through magnetic material imaging (MMI) is provided. The method includes generating a selection field to form a 1D field free region (FFR). The 1D FFR extends lengthwise along an imaging axis. The method also includes generating a drive field that combines with the selection field to move the 1D FFR through an object. The method also includes modifying a strength of the drive field to move the 1D FFR within the object in a direction that is perpendicular to the imaging axis. The method also includes detecting changes in magnetization from magnetic material located proximate to the 1D FFR within the object.

DETAILED DESCRIPTION

Embodiments described herein include systems and methods for imaging magnetic material in a spatial region. The systems and methods are based on a magnetic material imaging (MMI) modality, which may also be referred to as magnetic material tracking (MMT). MMI (or MMT) seeks to image a distribution of magnetic material (e.g., superparamagnetic iron oxide particles (SPIOs)) within the spatial region, such as within a patient's body. MMI detects changes in magnetization of the magnetic material that is proximate to a sensitive region (e.g., a field free point (FFP) or field free region (FFR)) that is generated by the MMI system. As used herein, the term "proximate to" includes the magnetic material being directly within or overlapping the sensitive region and also the magnetic material being suitably near the sensitive region. Magnetic material may be suitably near the sensitive region if an MMI system is capable of detecting changes in magnetization of the magnetic material for the purpose of imaging a region-of-interest (ROI) using MMI.

More specifically, magnetic material, such as SPIOs, can be spatially localized by applying a time-varying external magnetic field that has a designated or predetermined geometry. When exposed to the external magnetic field, domains in the magnetic material begin to align and the magnetization of the sample increases. Once all of the domains of the magnetic material are aligned with the external field, the sample is said to be "saturated" and further increases in the applied field produce minimal or undetectable changes in the magnetization. On the other hand, if a region of the applied field is relatively small such that the magnetic material is not saturated, perturbations in the region of the applied field may produce changes in magnetization, which can induce a measurable signal. For example, the measurable signal may be represented by a change in voltage or current. Thus, if the applied field is configured to have one or more high-field regions, wherein the magnetic material is saturated, and one or more low-field regions, wherein perturbations may produce changes in magnetization, an image can be constructed by moving (e.g., sweeping) the low-field region(s) throughout the object and detecting the changes in magnetization.

Accordingly, embodiments set forth herein are configured to generate a one-dimensional (1D) FFR and detect changes in magnetization of the magnetic material proximate to the 1D FFR. As used herein, a 1D FFR may be an elongated sensitive region that is substantially linear (e.g., straight) or curved. The 1D FFR may be formed by a selection field, which can be produced by a pair of Maxwell coils that extend parallel to each other along an imaging axis. In other embodiments, the selection field that forms the 1D FFR can be produced by an array of permanent magnets. By way of example only, the 1D FFR may have a cross-section transverse to the length of the 1D FFR that contains a low field region of about 0.5-5.0 $mm^2$ and is substantially uniform in size along the length of the 1D FFR. As described herein, the 1D FFR may then be moved by combining one or more drive fields. In particular embodiments, the drive fields are produced by coils that extend parallel to each other and along the imaging axis. The geometry of the coils may be similar to a butterfly or Helmholtz coil geometry, or determined through target field methods similar to those used in MRI gradient coil design. By flowing current through the coils, a movable 1D FFR can be created.

For example, the 1D FFR may be moved in one or more directions that are perpendicular to the imaging axis. The 1D FFR can be moved by modifying a direction and strength of the drive fields. In particular embodiments, the 1D FFR may be shaped because of elongated segments of the field-generating coils. Current flowing through the elongated segments generates the selection and drive fields that, in turn, provide a movable FFR.

The current flowing through the field-generating coils may be controlled (e.g., increased, decreased, or otherwise modified) to position and re-position the 1D FFR within the ROI. By continuously adjusting the drive field(s), the system can move (e.g., raster, sweep, and the like) the 1D FFR and obtain image data. The image data may be based on a measurable induced voltage or a measurable change in current caused by the changes in magnetization. The image data may then be used to generate viewable images (e.g., 2D images, 3D images, or 4D images). In particular embodiments, data acquisition and image generation occur in real-time thereby enabling a clinician or other qualified individual to use the imaging system for medical purposes. For example, the MMI system may be used to visualize an instrument, which has magnetic material and has been inserted into the patient, during a medical procedure (e.g., surgery). As one specific example, the MMI system may be used during a cardiac catheterization procedure in which a catheter that includes magnetic material is imaged or tracked by the MMI system while the catheter is within a patient's body. The magnetic material may be distributed throughout the catheter or located at predefined regions (e.g., tip, edges, and the like). In some cases, the MMI system may be used with other imaging modalities, such as x-ray. In that case, MMI images may be combined with x-ray images to co-register the catheter position with anatomy in real-time at a reduced dose.

One or more embodiments may be particularly suitable for tracking an instrument within a patient. The instrument may be doped or otherwise integrated with the magnetic material in a manner that minimizes exposure of the magnetic material to the patient. In such cases, the type of magnetic material integrated with the instrument may be configured in a manner that renders the instrument more easily detectable through MMI. For example, the size of the magnetic particles may be greater and/or smaller than the magnetic particles that are conventionally used or the composition of the magnetic particles may provide greater or smaller magnetic moments. In some cases, different magnetic materials (e.g., differing in particle size and/or type) may provide characteristic signatures that enable a system to distinguish the different magnetic materials.

Although particular embodiments may be suitable for tracking instruments in a patient, embodiments set forth herein are not limited to the tracking of instruments. For example, in some cases, the MMI systems and methods described herein may be used to image magnetic material that has been injected into a patient. In other embodiments, the MMI systems and methods described herein may be used to image magnetic material that is found in an inanimate object (e.g., luggage, shipping containers, etc).

In certain embodiments, a MMI system with a bi-planar, "c-arm" geometry is provided that is capable of 2D projection imaging. For example, the images may be of a surgical instrument that is integrated with (e.g., doped) or otherwise affixed to magnetic material. Conventional MPI systems utilize a sensitive point which is scanned over a volume to construct a 3D image. In contrast, embodiments described herein may generate 2D projection images by moving (e.g., scanning) a 1D FFR in two different directions that are orthogonal to the direction that the 1D FFR extends along. This procedure may be similar to X-ray fluoroscopy. Compared to the single sensitive point technology that is used in conventional MPI, imaging can be performed more rapidly with the 1D FFR, which may enable real-time tracking with high spatial resolution during a surgical procedure. If a three dimensional roadmap is desired, the c-arm could be rotated around the patient to take a series of 2D projections which can be reconstructed into a 3D image.

Figure 1:
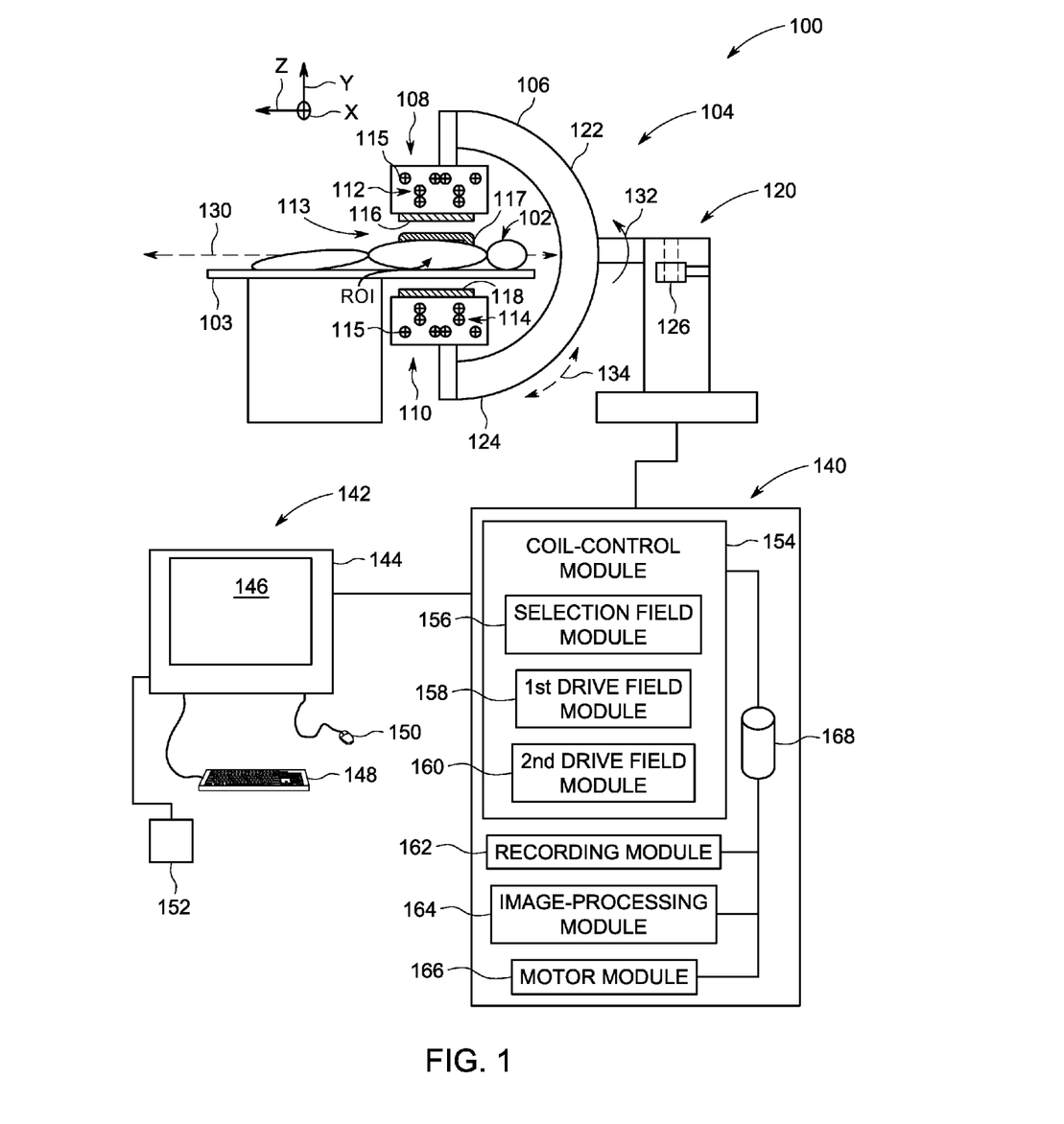
FIG. 1 illustrates a schematic block diagram of a magnetic material imaging (MMI) system in accordance with one embodiment.
Figure 2:
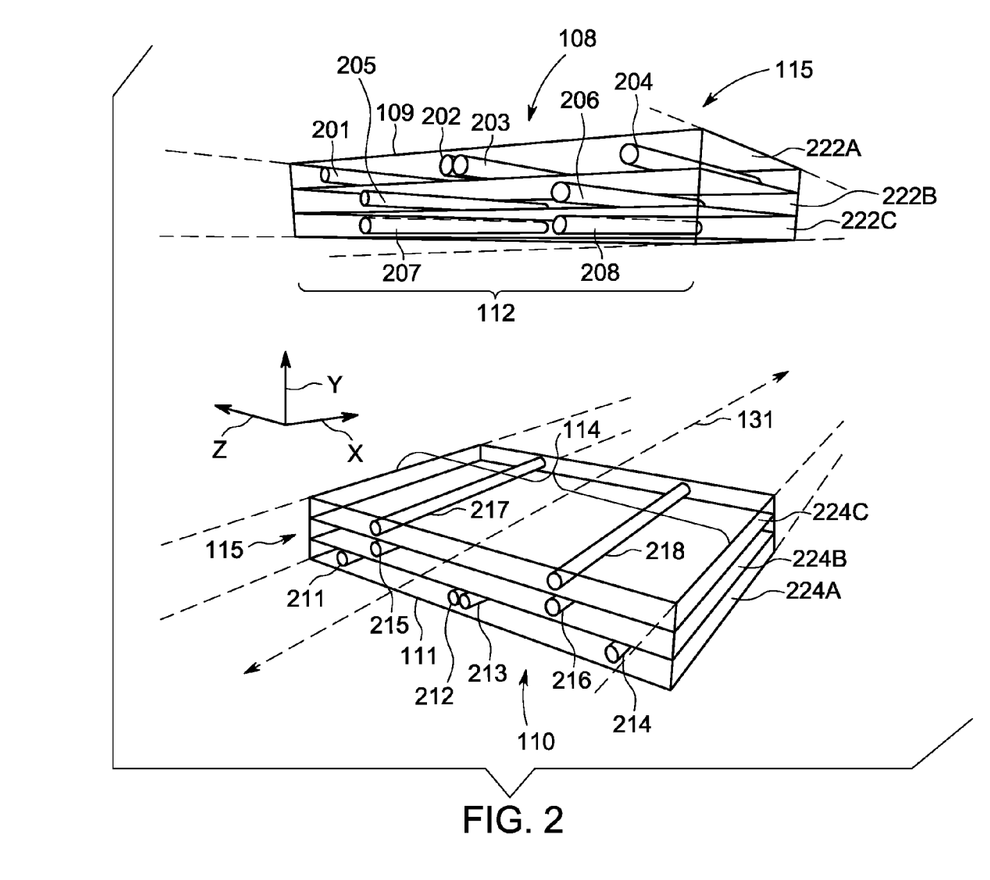
FIG. 2 is a schematic illustration showing elongated segments of field-generating coils that may be used with the MMI system of FIG. 1.

For instance, a 1D FFR may be generated by a bi-planar field generator, such as shown in FIGS. 1 and 2. The bi-planar geometry allows minimal interference of the imaging apparatus with the medical staff. The 1D FFR may be swept by applying a uniform magnetic field in the two orthogonal directions to produce a projection of the object along the axis of the 1D FFR. By sweeping the 1D FFR in two dimensions, the acquisition rate may be increased, relative to conventional single point MPI, and the specific absorption rate (SAR) may be decreased substantially. In such an embodiment, the resulting images may be 2D projections of a 3D object. Surgeons are already accustomed to operating with this type of visualization due to the pervasive use of X-ray fluoroscopy. If a 3D image is required, the MMI system can be rotated around the patient taking a series of projections. These 2D projections can then be combined to reconstruct a 3D image.

In some embodiments, the magnetic material may be injected into the patient. The magnetic material may be configured to be absorbed or particularly drawn to predetermined regions within the patient's body. In such embodiments, the magnetic material within the predetermined regions of the patient (e.g., particular tissue or anatomical structure) or within the bloodstream and the magnetic material in the instrument may be distinguished based on size and/or composition of the magnetic material.

Magnetic particle imaging (MPI) concepts are described in greater detail in T. Knopp, T. M. Buzug, *Magnetic Particle Imaging: An Introduction to Imaging Principles and Scanner Instrumentation* (2012), Chapter 2: "How Magnetic Particle Imaging Works," and Chapter 3: "How to Build an MPI Scanner," in which each of the chapters is incorporated by reference in its entirety for the purpose of understanding the embodiments described herein. MPI concepts with respect to field free lines are described in greater detail in Weizenecker et al., *Magnetic Particle Imaging Using a Field Free Line*, J. Phys. D: Appl. Phys. 41 (2008) and in Knopp et al., *Field-Free Line Formation in a Magnetic Field*, J. Phys. A: Math. Theor. 43 (2010), each of which is incorporated by reference in its entirety for the purpose of understanding the embodiments described herein. MMI systems and methods set forth herein are based on such MPI concepts.

At least one technical effect of embodiments described herein may include improved methods or systems for imaging magnetic material within a ROI and/or tracking an instrument having magnetic material. At least one technical effect may include obtaining 2D projection data of a patient and/or instrument. Another technical effect may include a MMI system that has a bi-planar C-arm geometry. Yet still another effect may include a reduction in acquisition time.

The following detailed description of various embodiments will be better understood when read in conjunction with the appended figures. To the extent that the figures illustrate diagrams of the functional blocks of the various embodiments, the functional blocks are not necessarily indicative of the division between hardware circuitry. Thus, for example, one or more of the functional blocks (e.g., modules, processing units, or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

FIG. 1 is a schematic diagram of a MMI system 100 formed in accordance with one embodiment. The MMI system 100 is configured to image magnetic material within an object 102. In the illustrated embodiment, the object 102 is a patient and, as such, will be referred to as the patient 102. The patient 102 may be human or an animal. However, it is understood that the object may not be human or animal in other embodiments. For example, the object may be any apparatus (e.g., luggage, shipping containers, etc.) in which it is desired to image magnetic material within the object.

In some embodiments, the magnetic material is part of an instrument (e.g., catheter or other surgical device) that is inserted into the body of the patient 102. The MMI system 100 may be used to track the instrument. In such embodiments, the instrument may be inherently magnetic or may be modified to include the magnetic material. For example, the instrument can have magnetic particles inserted into the instrument or the instrument can be coated with magnetic particles. The magnetic particles may be characterized as superparamagnetic iron oxide particles (SPIOs). In other embodiments, the magnetic material may be a tracer or, more specifically, a substance that facilitates the imaging process. For example, the substance may include biocompatible magnetic particles that have been deposited (e.g., injected or otherwise positioned within the patient 102). Resovist® is a contrast agent that includes magnetic nanoparticles that may have a suitable magnetic moment and relaxation time for MMI. However, such nanoparticles are only examples of particles that may be suitable for MMI and other particles may exist or be developed for MMI.

As shown in FIG. 1, the MMI system 100 includes an imaging assembly or imager 104 that is configured to image the patient 102 as described herein. In the illustrated embodiment, the imaging assembly 104 has an open bi-planar configuration with a C-arm 106. However, the MMI system 100 and the imaging assembly 104 may have various configurations and embodiments that are not limited to the bi-planar configuration shown in FIG. 1. As shown, the imaging assembly 104 includes first and second field units 108, 110 that are spaced apart from each other. The space between the field units 108, 110 may be sufficient for the patient 102 and a table 103 supporting the patient 102 to be positioned therebetween. Each of the field units 108, 110 includes first and second sets 112, 114 of field-generating coils 115 respectively. Optionally, the field units 108, 110 may include permanent magnets for generating a selection field as described herein. The field units 108, 110 are configured to generate magnetic fields for imaging the patient 102 through MMI.

As will be described in greater detail below, the sets 112, 114 of field-generating coils 115 may have corresponding elongated segments. The elongated segments extend into and out of the page in FIG. 1, but other configurations may be used. Although not shown, the field-generating coils 115 may include turns such that a field-generating coil includes more than one elongated segment. As such, the same current may flow through more than one elongated segment. The elongated segments in each of the field units 108, 110 may extend generally parallel to one another.

The imaging assembly 104 also includes a detection assembly 113 that, in some embodiments, may be referred to as a receiver or receiving assembly. In the illustrated embodiment, the detection assembly 113 includes recording coils 116-118. In other embodiments, the detection assembly 113 may include other components for detecting magnetization changes, such as an antenna or magnetometer (e.g., flux-gate, hall probe, atomic magnetometer, diamond magnetometer, magneto-resistive sensor, giant magneto-resistive sensor, anisotropic magneto-resistive sensor, SQUID). The recording coils 116-118 are positioned relative to the patient 102 to detect changes in magnetization of magnetic material located in the patient 102. For example, the recording coils 116-118 may detect an induced voltage that is caused by the changes in magnetization. In other embodiments, a change in current may be detected. In the illustrated embodiment, the recording coils 116, 118 are attached to the field units 108, 110, respectively, but the recording coils 116, 118 may have other locations relative to the patient 102. Each of the recording coils 116, 118 may have a fixed position that is separate from the field units 108, 110. For example, the recording coil 117 extends along a side of the patient 102 and the table 103.

Optionally, the imaging assembly 104 includes a positioning system 120 that move the field units 108, 110 with respect to the patient 102. For instance, the positioning system 120 may include first and second arms 122, 124 that support the first and second field units 108, 110, respectively. The arms 122, 124 in the illustrated embodiment are shaped to form a C-arm geometry, although other geometries may be used. The positioning system 120 may include a mechanical device, such as a motor 126, for moving (e.g., rotating, sliding) the arms 122, 124 and, hence, the field units 108, 110. For instance, the field units 108, 110 may be rotated about an examination axis 130, moved parallel to examination axis 130, moved in a direction perpendicular to the examination axis 130, or a combination thereof. In other embodiments, the mechanical device may be similar to a drafting light that enables a person to manually move the arms 122, 124. As shown in FIG. 1, the examination axis 130 extends longitudinally along a length or height of the patient 102. The arms 122, 124 may be rotated as indicated by the arrow 132 such that the arms 122, 124 rotate about the examination axis 130. In alternative embodiments, the arms 122, 124 may be rotated about an axis that intersects the examination axis 130. As shown by the arrow 134, the arms 122, 124, may be moved within a plane defined by the page (e.g., a plane that coincides with or is parallel to the examination axis 130). Moreover, in some embodiments, the positioning system 120 may be shifted or moved along the ground to reposition the detection assembly 120 with respect to the patient 102.

As shown, the imaging assembly 104 is operably connected (e.g., with physical wires or wirelessly connected) to a computing system 140. The computing system 140 is operably connected to a user interface 142 that enables an operator to control at least some of the operations of the system 100. The user interface 142 may include hardware, firmware, software, or a combination thereof that enables an individual (e.g., an operator) to directly or indirectly control operation of the MMI system 100 and the various components thereof. As shown, the user interface 142 includes a display device 144 having a display area 146. In some embodiments, the user interface 142 may also include one or more input devices, such as a physical keyboard 148, mouse 150, and/or touchpad 152.

In some embodiments, the display device 144 may include a touch-sensitive display (e.g., touchscreen) that can detect a presence of a touch from the operator on the display area 146 and can also identify a location of the touch in the display area 146. The touch may be applied by, for example, at least one of an individual's hand, glove, stylus, or the like. As such, the touch-sensitive display may also be characterized as an input device that is configured to receive inputs from the operator. The display device 144 may also communicate information to the operator by displaying the information to the operator or by displaying MMI images to the operator. The MMI images may be combined with other types of images, such as x-ray images. The display device 144 is configured to present information to the operator during the imaging session.

The computing system 140 may include a plurality of modules. The modules may be part of a single processing unit (e.g., processor) or distributed across multiple processing units (e.g., multi-processor). As used herein, the terms "computing system" or "module" may include a hardware and/or software system that operates to perform one or more functions. For example, a computing system or module may include a computer processor, controller, or other logic-based device that performs operations based on instructions stored on a tangible and non-transitory computer readable storage medium, such as a computer memory. Alternatively, a computing system or module may include a hard-wired device that performs operations based on hard-wired logic of the device. The computing system and modules shown in the attached figures may represent the hardware that operates based on software or hardwired instructions, the software that directs hardware to perform the operations, or a combination thereof.

The computing system 140 is configured to control operation of the MMI system 100 and, more specifically, the imaging assembly 104. To this end, the computing system 140 and the modules may be configured to execute one or more predetermined algorithms. For example, the computing system 140 may include a coil-control module 154 that is configured to control operation of the sets 112, 114 of field-generating coils 115. The coil-control module 154 may include sub-modules, such as a selection field module 156, a first drive field module 158, and a second drive field module 160. The first and second drive field modules 158, 160 may be referred to as x- and y-drive field modules in some instances. The coil-control module 154 (and the sub-modules) is configured to control the flow of current through the field-generating coils 115. As described in greater detail below, the field-generating coils 115 may be designated for predetermined operations or functions. For example, a group of the field-generating coils 115 may function to generate a drive field that moves the 1D FFR in one direction whereas another group of the field-generating coils 115 may function to generate a drive field that moves the 1D FFR in a different direction. The flow of current through the field-generating coils 115 may be pursuant to one or more algorithms.

The computing system 140 also includes a recording module 162. The recording module 162 is operably connected to the detection assembly 113 (e.g., recording coils 116-118) and is configured to receive data from the detection assembly 113 that represents detection of magnetization changes. For example, the data may represent a voltage induced in the recording coils by the changes in magnetization within a volume of the patient or change in current. The recording module 162 may also control operation of the recording coils 116-118 to facilitate detection of the magnetization changes.

The computing system 140 also includes an image-processing module 164. The image-processing module 164 receives image data (e.g., MMI data from the recording module 162) and processes the image data. For instance, the image-processing module 164 may include one or more components for filtering and/or amplifying the signals to generate the images (e.g., projections). For example, the image-processing module 164 may process the MMI data to generate image frames of the magnetic material, such as an instrument or anatomical structure of the patient. The image-processing module 164 may communicate with the display device 144 to display the MMI images. In some cases, the images obtained by the imaging assembly 104 are 2D projections. The 2D projections may be processed into 2D images and/or processed into 3D images by acquiring a series of 2D images at various projection angles.

In some embodiments, the image-processing module 164 may combine the MMI data with data from other imaging modalities, such as x-ray data, ultrasound data, MRI data, and the like. The image-processing module 164 may process the data from multiple modalities to form a combined image. For example, the combined image may show an anatomical structure as captured through X-ray imaging and also show an instrument as captured through MMI. In some cases, the instrument may appear to be overlaid with the anatomical structure. In other embodiments, the image-processing module 164 may process the data separately and display the images on the display device 144 as separate images (e.g., side-by-side).

A motor module 166 may also be part of the computing system 140. The motor module 166 may command the positioning system 120 to move the field units 108, 110 in accordance with a predetermined protocol. The positioning system 120 may communicate with the coil-control module 154 and/or the recording module 162 to image the patient 102 in accordance with the protocol. For example, the motor module 166 may command the positioning system 120 to rotate about the examination axis 131 at a designated speed so that the imaging assembly 104 can capture certain MMI images of the patient 102. The motor module 166 may also command the positioning system 120 to move the field units parallel to the examination axis 131. Also shown in FIG. 1, each of the modules may utilize or communicate with a memory 168.

In some embodiments, the computing system and/or the modules of the computing system include circuitry that is configured to achieve the actions or functions described herein. For example, the circuitry may be configured to receive inputs (e.g., from a user of the system or from another portion of the computing system), process the inputs, and provide designated outputs. The designated outputs may include signals that have instructions for performing designated actions. The actions may be physical actions or otherwise detectable actions, such as moving the field units 108, 110 or increasing/decreasing the current within field-generating coils 115. The actions may also include instructions for furthering processing. By way of one example, the first and second drive field modules 158, 160 may transmit instructions that cause a select number of field-generating coils to be activated in accordance with a predetermined protocol. In some embodiments, the modules described herein may also be referred to as circuits or circuitry.

FIG. 2 is a schematic illustration of the field units 108, 110 and, more specifically, the sets 112, 114 of the field-generating coils 115. Only portions of the field-generating coils 115 are shown in FIG. 2. For example, each of the portions shown includes an elongated segment. However, it is understood that the elongated segments may extend longer than shown in FIG. 2 and that the field-generating coils 115 may be shaped in various geometries. Each of the elongated segments generates a magnetic field when current flows through the respective elongated segment. Collectively, the magnetic fields of the elongated segments may generate drive fields for moving the 1D FFR. For clarity, the elongated segments of the first set 112 are referenced as elongated segments 201-208, and the elongated segments of the second set 114 are referenced as elongated segments 211-218. By way of example, the elongated segments 201-208, 211-218 may extend lengthwise between about 20-50 cm or, more particularly, between about 28 cm to about 42 cm.

The field units 108, 110 may include unit housings or bodies 109, 111 that surround and contain the corresponding field-generating coils 115 having the elongated segments 201-208, 211-218, respectively. In the illustrated embodiment, the unit housings 109, 111 are generally block shaped, but other shapes and configurations may be used. The field units 108, 110 are located on opposite sides of the ROI.

As shown in FIG. 2, the elongated segments 201-208, 211-218 may be positioned relative to each other to form coil layers. As used herein, the elongated segments of a designated "coil layer" are co-planar (e.g., extend along a common plane). In the illustrated embodiment, the elongated segments of one coil layer do not intersect or extend into the elongated segments of another layer. By way of example, the field unit 108 includes coil layers 222A-222C and the field unit 110 may include coil layers 224A-224C. The coil layer 222A includes the elongated segments 201-204; the coil layer 222B includes the elongated segments 205, 206; and the coil layer 222C includes the elongated segments 207, 208. The coil layer 224A includes the elongated segments 211-214; the coil layer 224B includes the elongated segments 215, 216; and the coil layer 224C includes the elongated segments 217, 218. As shown, the elongated segments 201-208 extend substantially parallel to one another, and the elongated segments 211-218 extend substantially parallel to one another. In particular embodiments, the elongated segments 201-208 and 211-218 extend parallel to one another. The elongated segments 201-208, 211-218 may extend generally along or parallel to an imaging axis 131, which is perpendicular to the examination axis 130 (FIG. 1) in the illustrated embodiment. In other embodiments, the imaging axis 131 may coincide or extend parallel to the examination axis 130.

When current flows through the elongated segments 201-208, 211-218, each of the elongated segments 201-208, 211-218 may generate a distinct magnetic field. The magnetic field encircles the elongated segment 201-208, 211-218 in a direction that is based on a direction of current flow. Accordingly, each of the elongated segments 201-208, 211-218 may generate a magnetic field that, depending on the direction of current flow, combine with the magnetic field of the other elongated segment. As used herein, "combine" includes more than one magnetic field being applied to a common region whether or not the applied magnetic fields counteract each other or enhance each other.

In some embodiments, one or more of the elongated segments are part of the same electrical pathway such that current flowing through a first elongated segment also flows through a second elongated segment. For instance, a single wire may extend through the layer 222A and be wrapped about to form the elongated segments 201-204. A single wire may also extend through the layer 222C and be wrapped about to form the elongated segments 207, 208. Moreover, some of the layers may be connected in series. For example, the elongated segments 211-214 of the coil layer 224A may be in series with the elongated segments 201-204 of the coil layer 222A.

Figure 3:
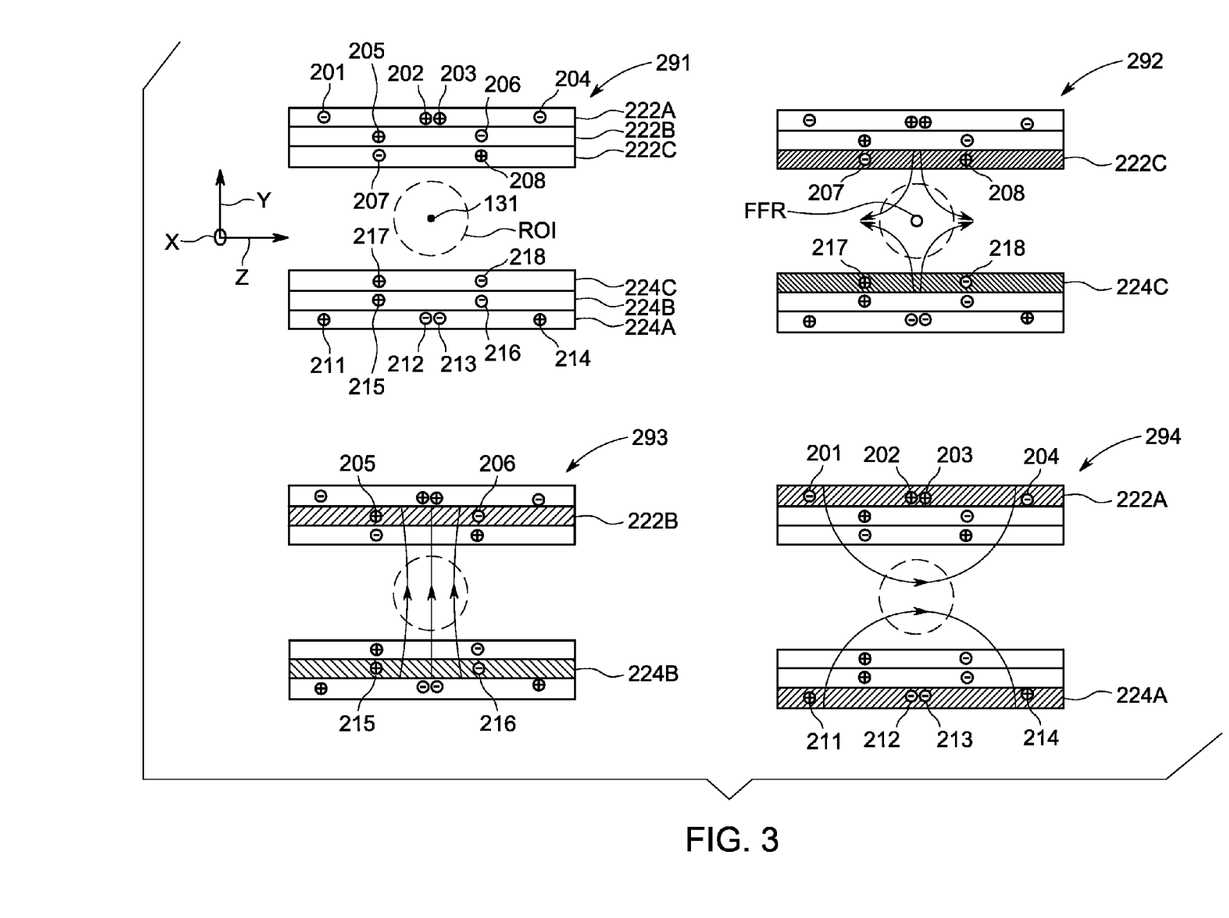
FIG. 3 illustrates multiple end views of the elongated segments of FIG. 2 in accordance with one embodiment when different magnetic fields are applied.

FIG. 3 illustrates different end views of the coil layers 222A-222C, 224A-224C and demonstrates how selective activation of the field-generating coils 115 (FIG. 1) that correspond to the elongated segments 201-208, 211-218 may generate one or more magnetic fields that is to be used during MMI. In particular, FIG. 3 illustrates representative field lines of a selection field 292, a first drive field 293, and a second drive field 294. FIG. 3 also illustrates a base field 291 in which none of the magnetic fields 292-294 is activated. Although FIG. 3 separately illustrates the selection field 292 and the first and second drive fields 293, 294, the selection field 292 and the first and second fields 293, 294 may be generated simultaneously to move the 1D FFR. More specifically, strengths of the magnetic fields 292-294 may be controlled to move the 1D FFR in a predetermined manner.

With respect to the base field 291, none of the elongated segments 201-208, 211-218 is activated. A dashed circle represents the ROI of the patient 102 (FIG. 1). In some embodiments, the imaging axis 131 may extend approximately through a center of the ROI. For example, the imaging axis 131 extends into and out of the page through a center of the dashed circle in FIG. 3. Each of the field-generating coils is marked as being "+" or "−". The + sign indicates that the direction of current flow is into the page, and the − sign indicates that direction of current flow is out of the page. As shown, the elongated segments 202, 203, 205, 208, 211, 214, 215, and 217 have a + flow, and the elongated segments 201, 204, 206, 207, 212, 213, 216, and 218 have a − flow.

When the selection field 292 is applied, the elongated segments 207, 208 of the coil layer 222C and the elongated segments 217, 218 of the coil layer 224C are activated. The coil layers 222C and 224C (or the elongated segments 207, 208, 217, 217) may constitute a selection-field generator, which in some cases may be referred to as a static magnetic field generator. As demonstrated by the field lines, an FFR may be formed when the selection field is applied. The strength of the selection field outside of the 1D FFR has a relatively high magnetic field, but the strength of the selection field at the 1D FFR is relatively low or zero.

When the first drive field 293 is applied, the elongated segments 205, 206 of the coil layer 222B and the elongated segments 215, 216 of the coil layer 224B are activated. The coil layers 222B and 224B (or the elongated segments 205, 206, 215, 216) may constitute a first drive-field generator (e.g., an AC magnetic field generator). As demonstrated by the field lines, the first drive field 293 is substantially homogenous and extends along the y-axis. In a similar manner, the second drive field 294 may be applied. As shown, the elongated segments 201-204 of the coil layer 222A and the elongated segments 211-214 of the coil layer 224A are activated for the second drive field 294. The coil layers 222A and 224A (or the elongated segments 201-204, 211-214) may constitute a second drive-field generator (e.g., an AC magnetic field generator). The second drive field 294 is substantially homogenous and extends along the z-axis.

In some embodiments, the current may flow in either direction. For example, the direction of current flow may be reversed through the elongated segments 201-208, 211-218 in FIG. 3. More specifically, the direction of current flow through the elongated segments 201-204 and 211-214 may be reversed thereby enabling movement of the 1D FFR in an opposite direction along the z-axis. Likewise, the direction of current flow through the elongated segments 205, 206 and 215, 216 may be reversed thereby enabling movement of the 1D FFR in an opposite direction along the y-axis.

Although FIG. 3 illustrates a particular configuration of the field-generating coils (i.e., elongated segments), it is understood that a variety of configurations may be used to provide the magnetic fields that generate the 1D FFR. For example, FIG. 3 illustrates one cross-section of the coil layers 222A-222C, 224A-224C. In some embodiments, the positional relationships shown in FIG. 3 among the elongated segments may be maintained throughout (e.g., along the imaging axis). In other embodiments, however, the positional relationships among the elongated segments may change as the cross-section moves along the imaging axis. For example, the elongated segments 207, 208 may move closer to or further away from each other.

Figure 4:
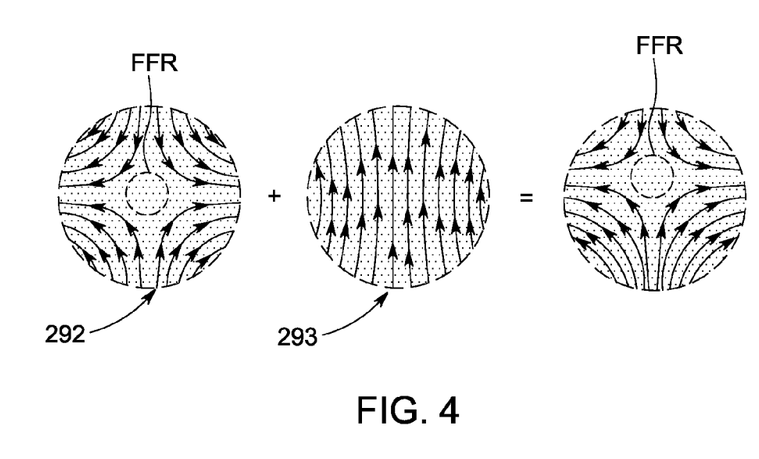
FIG. 4 illustrates movement of a 1D field-free region (FFR) in a first direction by applying a selection field and a first drive field.
Figure 5:
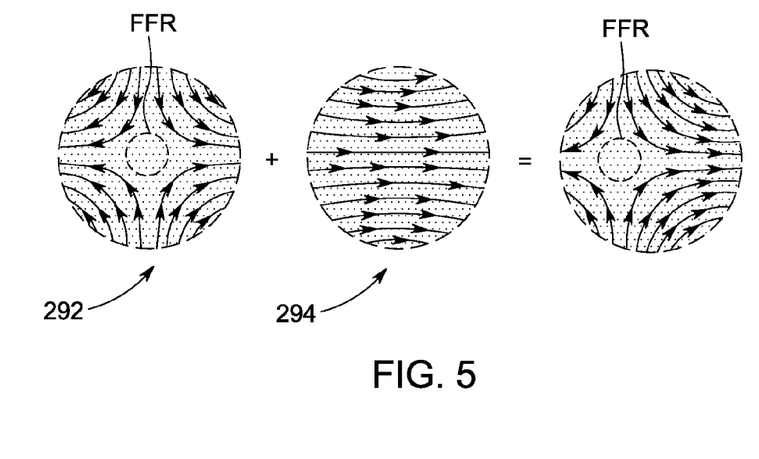
FIG. 5 illustrates movement of the 1D FFR in two directions by applying a selection field and two different drive fields.

FIGS. 4 and 5 illustrate movement of the 1D FFR in first and second directions, respectively. By controlling the activation, strength, and direction of the first and second drive fields 293, 294 when the selection field 292 is applied, the 1D FFR may be moved or shifted along the y-axis, along the z-axis, or both. For example, FIG. 4 shows a portion of representative field lines associated with the selection field 292 and a portion of representative field lines associated with the first drive field 293. When the selection field 292 and the first drive field 293 are simultaneously applied and therefore combined with respect to each other, the 1D FFR may be moved vertically along the y-axis. As shown in FIG. 5, when the selection field 292 and the second drive field 294 are simultaneously applied and therefore combined with respect to each other, the 1D FFR may be moved laterally along the z-axis. As such, the 1D FFR may be selectively moved by applying the first drive field and/or second drive field and the amount of such movement may be based on the strength of the corresponding drive field(s). Thus, a 1D FFR may be moved through a ROI in the patient. As the 1D FFR is moved, signals from the magnetic particles in the ROI may be detected and image data may be generated therefrom.

Figure 6:
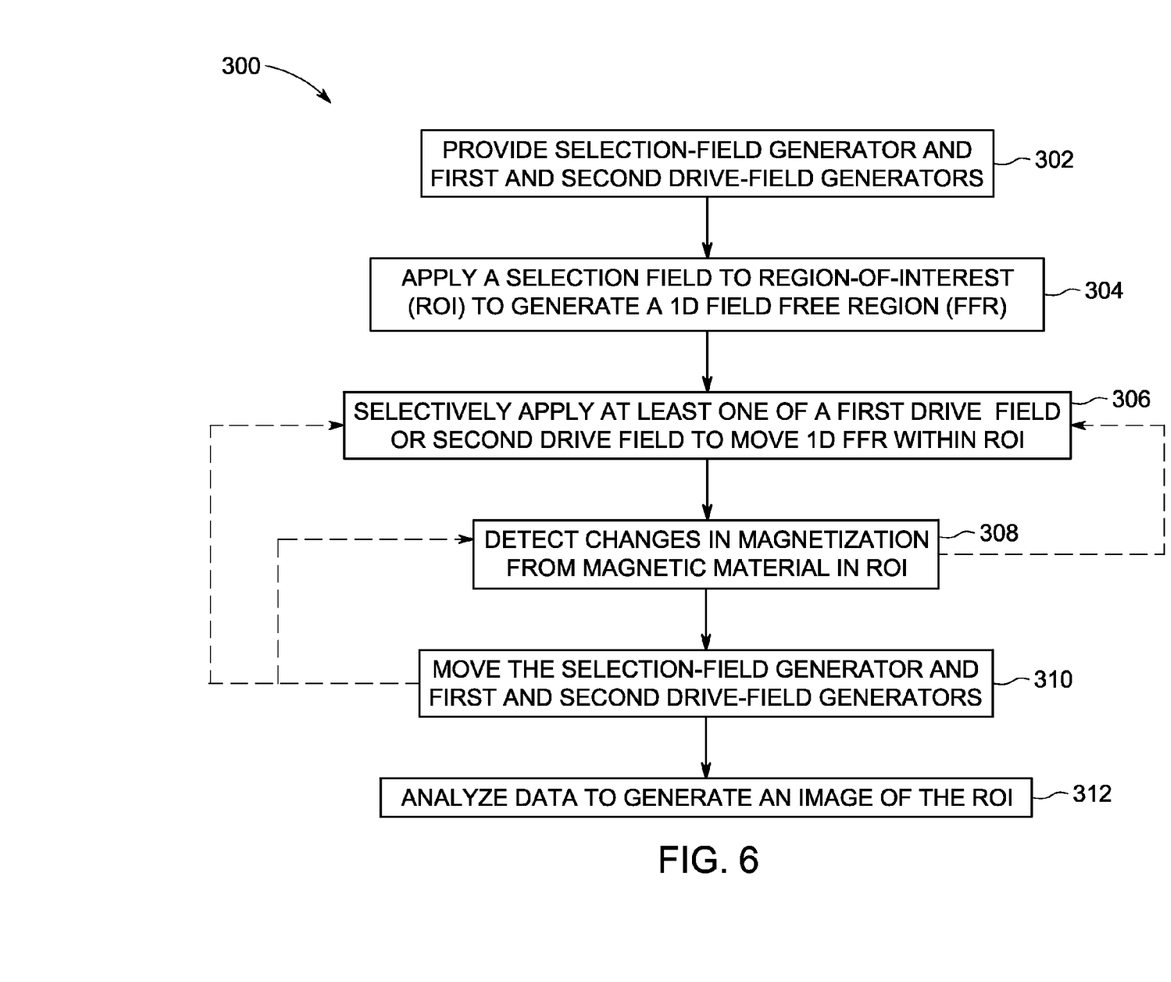
FIG. 6 is a flowchart illustrating a method of imaging a region-of-interest (ROI) with MMI.

FIG. 6 is a flowchart illustrating a method 300 of imaging a region-of-interest (ROI) with MMI. The ROI may be within an object and, in particular embodiments, the object is a patient. The method 300, for example, may employ structures or aspects of various embodiments (e.g., systems and/or methods) discussed herein. In various embodiments, certain steps (or operations) may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion.

The method 300 may include providing (at 302) a selection-field generator and one or more drive-field generators. The selection-field generator may be an array of field-generating coils having elongated segments that extend parallel to one another. Alternatively or additionally, an array of permanent magnets may be positioned relative to one another to generate a selection field as described herein. The drive-field generator(s) may be an array of field-generating coils in which current flow through the field-generating coils is capable of being controlled (e.g., increased, decreased, frequency changed, etc.).

The method 300 may also include applying (at 304) a selection field to a ROI in the object to generate a 1D FFR. The selection field may be generated by flowing or causing current to flow through designated field-generating coils or, alternatively or additionally, by positioning permanent magnets in designated positions with respect to one another. The 1D FFR may extend lengthwise along an imaging axis. The imaging axis may be parallel to an examination axis, which a patient may lay lengthwise along, or may extend in a non-parallel direction. For example, the imaging axis may extend perpendicular to the examination axis.

The method 300 also includes selectively applying (at 306) at least one of a first drive field or a second drive field to move the 1D FFR within ROI. More specifically, current may be controlled to flow through designated elongated segments of field-generating coils to effectively generate one or more drive fields. Strengths of the drive fields may be controlled by increasing or decreasing the flow of current through the elongated segments.

In particular embodiments, the drive fields are selectively controlled to move the 1D FFR in a designated manner. For example, the drive fields may be controlled to move the 1D FFR through the spatial region of the ROI. The direction of movement may be perpendicular to the imaging axis. The movement may be back and forth along different planes that, when stacked, form a 2D projection within the ROI. More specifically, the 1D FFR may be electronically swept (e.g., by controlling the flow of current) along a first plane, electronically shifted into a different second plane, and electronically swept back again through the second plane. This step may be repeated until a desired 2D projection is obtained. Accordingly, embodiments described herein may move the 1D FFR through electronic rasterization. In particular embodiments, it is not necessary to move the patient or object during an imaging session.

At 308, changes in magnetization of magnetic material may be detected. The changes may be caused by movement of the 1D FFR and/or by transmitting perturbation signals into the 1D FFR that cause the changes in the magnetization. The changes may induce voltage in, for example, a recording coil thereby detecting the change.

Optionally, at 310, the selection-field generator and the first and second drive-field generators may be moved (e.g., rotated, shifted, and the like) with respect to the ROI. As one example, the 1D FFR may be rotated within the ROI by rotating the selection-field generator and the first and second drive-field generators. Depending upon the orientation of the 1D FFR with respect to the ROI, the 1D FFR may be rotated within an orthogonal plane that intersects an examination axis that a patient or object lies along. In this manner, "slices" of the ROI may be obtained when the 1D FFR is rotated and the magnetization changes at subsequent rotational positions are detected. For example, after fully rotating and obtaining one slice, the first and second drive fields may be modified (at 306) to move the 1D FFR to a different position. With the new 1D FFR position, the 1D FFR may again be rotated to obtain an adjacent slice of the ROI. By repeating these steps, a stack of slices (e.g., 2D projections) of the ROI may be obtained. In some embodiments, the 1D FFR may be electronically moved while also be rotated. At 312, the data may be analyzed to generate images (e.g., 2D or 3D images).

In one embodiment, a system for real-time tracking of magnetically doped surgical instruments in-vivo is provided. The system may include a bi-planar static magnetic field generator that is capable of producing a 1D FFR in which the magnetic field along a line through the 1D FFR is zero or substantially zero and the volume surrounding the line has a value greater than zero. The system may also include two AC magnetic field generators, which may also have a bi-planar configuration, in which each AC magnetic field generator produces a uniform field oriented in a direction perpendicular to the 1D FFR. The AC magnetic field generators may be operated independently with respect to each other and/or the static magnetic field generator such that that the 1D FFR can be moved (e.g., scanned, translated) through an imaging volume. In such embodiments, one or more surgical instruments may be labeled with magnetic material and a receiver (e.g., detection assembly) may be configured to detect the changing magnetization of the surgical instrument. The system may also include a computing system that receives the raw image data from the receiver and reconstructs 2D projections of the surgical instrument.

Optionally, the static magnetic field generator may be an electromagnet or a permanent magnet. The AC magnetic field generators may be electromagnets. The surgical instrument may contain or be attached to a polymer matrix having superparamagnetic iron oxide (SPIO). In some embodiments, a solution having SPIO may be stored within the surgical instrument.

In particular embodiments, the surgical instrument may be formed with the SPIO such that the housing or other function components of the surgical instrument include the SPIO. By way of example, the surgical instrument may be a catheter or a guidewire. The surgical instrument may also include ferromagnetic or ferrimagnetic material.

In certain embodiments, the receiver is a coil which is inductively coupled to the magnetic material in the surgical instrument. In other embodiments, the receiver is a magnetometer (flux-gate, hall probe, atomic magnetometer, diamond magnetometer, magneto-resistive sensor, giant magneto-resistive sensor, anisotropic magneto-resistive sensor, SQUID, etc . . . )

In another embodiment, a method for real time visualization of a local anatomy of a patient in relation to a surgical instrument is provided. The method may include releasing magnetic material from a magnetically doped surgical instrument into a body of a patient. The method may also include generating a static magnetic field with 1D FFR and sweeping the 1D FFR in the field of view through the use of AC magnetic field generators. The method may also include detecting a change in the magnetization of both the magnetic material in the surgical instrument and the magnetic material that was released into the body. The method may also include reconstructing a two-dimensional projection of the surgical instrument and the local anatomy. Optionally, the magnetic material, once released, may be targeted to a specific anatomy.

In another embodiment, a method for three dimensional visualization of magnetic material is provided. The method may include acquiring a series of 2D projection images with a bi-planar MMT system while rotating magnetic field generators around the patient. The method may also include reconstructing the 2D images to form a 3D image.

It is noted that the MMI systems described herein may be used in conjunction with other imaging systems. For instance, the MMI system can be part of a multi-modality imaging system that includes an imaging system of another modality. Examples of such other imaging systems include x-ray fluoroscopy, nuclear imaging, a magnetic resonance imaging (MRI) system, computed tomography (CT) system, positron emission tomography (PET) system, a PET/CT system, and single photon emission computed tomography (SPECT) system.

For example, in one embodiment, a method for real time visualization of an anatomy in relation to a surgical instrument is provided. The method may include acquiring an image of magnetically doped surgical instrument using magnetic material tracking (MMT). The method may include simultaneously acquiring an image of the anatomy with a real time ultrasound and integrating the MMT image with the RT-US image data to construct a registered image of the surgical instrument amidst the surrounding anatomy.

In yet another embodiment, a method for real time high resolution/high contrast visualization of anatomy in relation to a surgical instrument is provided. The method may include simultaneous acquisition of ultrasound images with high resolution/high contrast MR images using an MR compatible ultrasound transducer. The method may also include mapping the MR images to the lower resolution ultrasound images and simultaneous acquiring magnetically doped surgical instruments with MMT and real time ultrasound. The method also includes mapping of the MMT images to the RT-US images followed by subsequent mapping of the RT-US images to the high resolution MR images resulting in an MMT image being registered with the high resolution/high contrast MR image. Optionally, the ultrasound and MR images are acquired in cine and mapped spatially and temporally, therefore resolving motion with real time registration of MMT images with real time high resolution/high contrast MR images.

In one embodiment, a magnetic material imaging (MMI) system is provided that includes first and second sets of field-generating coils. Each of the field-generating coils of the first and second sets has an elongated segment that extends along an imaging axis of the medical imaging system. The imaging axis extends through a region-of-interest (ROI) of an object. The elongated segments of the first set of field-generating coils are positioned opposite the elongated segments of the second set of field-generating coils and the ROI is located between the first and second sets of field-generating coils. The MMI system also includes a coil-control module configured to control a flow of current through the first and second sets of field-generating coils to generate a selection field and to generate a drive field. The selection and drive fields combine to form a movable 1D field free region (FFR) that extends through the ROI. The MMI system also includes a detection assembly that is positioned relative to the ROI to detect changes in magnetization of magnetic material located proximate to the 1D FFR in the ROI.

In one aspect, the coil-control module is configured to control the flow of the current through the first and second sets of field-generating coils to move the 1D FFR back and forth through the ROI.

In another aspect, the elongated segments for each of the first and second sets are positioned relative to each other to form multiple coil layers in which each coil layer includes a plurality of the elongated segments.

In another aspect, the selection field is configured to be generated by a plurality of the elongated segments from the first set of field-generating coils and a plurality of the elongated segments from the second set of field-generating coils. The drive field is configured to be generated by a plurality of the elongated segments from the first set of field-generating coils and a plurality of the elongated segments from the second set of field-generating coils.

In another aspect, the drive field is a first drive field and the coil-control module is configured to control the flow of the current through the first and second sets of field-generating coils to generate a second drive field. Each of the first and second drive fields is configured to move the 1D FFR in a different direction within the ROI.

In another aspect, the MMI system also includes an image-processing module configured to receive image data from the detection assembly. The image data is based on measurements of the changes in magnetization. For instance, the magnetic material may be part of an instrument. The changes in magnetization within the ROI may be caused by the magnetic material of the instrument, and the image-processing module may be configured to generate a representation of the instrument within the ROI.

In another embodiment, a magnetic material imaging (MMI) system is provided that includes first and second field units that are spaced apart from each other. Each of the first and second field units includes field-generating coils that have corresponding elongated segments. The elongated segments of the first and second field units extend generally along one another. The MMI system also includes a coil-control module that is configured to control a flow of current through the field-generating coils to generate a 1D free field region (FFR) between the first and second field units. The MMI system also includes a detection assembly that is positioned relative to the object to detect changes in magnetization of magnetic material located proximate to the 1D FFR. The MMI system also includes a positioning system that has first and second arms that are coupled to and support the first and second field units, respectively. The positioning system is configured to move the first and second field units with respect to a patient.

In one aspect, the MMI system has an open bi-planar C-arm geometry.

In another aspect, the coil-control module is configured to control the flow of the current through the field-generating coils to generate a selection field and to generate one or more drive fields. The selection and drive fields combine to form the 1D FFR. For instance, the 1D FFR may extend lengthwise along an imaging axis. The coil-control module may be configured to modify the selection and drive fields to move the 1D FFR such that the 1D FFR moves in a direction that is perpendicular to the imaging axis. Optionally, the coil-control module may be configured to move the 1D FFR as the positioning system moves the first and second field units with respect to the object.

In another aspect, the MMI system includes an image-processing module that is configured to receive image data from the detection assembly and generate a MMI image. The MMI image is based on measurements detected by the detection assembly.

In one aspect, the MMI system also includes a display device configured to display the MMI image.

In another embodiment, a method of imaging a region-of-interest (ROI) in a patient through magnetic material imaging (MMI) is provided. The method includes generating a selection field to form a 1D field free region (FFR). The 1D FFR extends lengthwise along an imaging axis. The method also includes generating a drive field that combines with the selection field to move the 1D FFR through an object. The method also includes modifying a strength of the drive field to move the 1D FFR within the object in a direction that is perpendicular to the imaging axis. The method also includes detecting changes in magnetization from magnetic material located proximate to the 1D FFR within the object.

In one aspect, modifying the strength of the drive field to move the 1D FFR includes moving the 1D FFR in the direction that is perpendicular to the imaging axis.

In another aspect, the drive field is a first drive field and the direction is a first direction. The method also includes generating a second drive field and modifying a strength of the second drive field to move the 1D FFR within the object in a second direction that is perpendicular to the imaging axis.

In another aspect, the imaging axis extends substantially perpendicular to an examination axis and the selection and drive fields are generated by field-generating coils having elongated segments. The method also includes moving the field-generating coils to move the 1D FFR within a plane that is orthogonal to the examination axis.

In another aspect, modifying the strength of the drive field to move the 1D FFR includes moving the 1D FFR as the 1D FFR is being rotated.

In another aspect, the method includes displaying two-dimensional or three-dimensional MMI images of the object.

In accordance another embodiment, a non-transitory computer readable medium for imaging a region-of-interest (ROI) in a patient through magnetic material imaging (MMI) is provided. The computer readable medium includes instructions to command the processor to generate a selection field to form a 1D field free region (FFR). The 1D FFR extends lengthwise along an imaging axis. The computer readable medium also includes instructions to command the processor to generate a drive field that combines with the selection field to move the 1D FFR through an object. The computer readable medium also includes instructions to command the processor to modify a strength of the drive field to move the 1D FFR within the object in a direction that is perpendicular to the imaging axis. The computer readable medium also includes instructions to command the processor to detect changes in magnetization from magnetic material located proximate to the 1D FFR within the object.

As used herein, an element or step recited in the singular and proceeded with the word "a" or "an" should be understood as not excluding plural of said elements or steps, unless such exclusion is explicitly stated. Furthermore, references to "one embodiment" of the presently described inventive subject matter are not intended to be interpreted as excluding the existence of additional embodiments that also incorporate the recited features. Moreover, unless explicitly stated to the contrary, embodiments "comprising," "comprises," "including," "includes," "having," or "has" an element or a plurality of elements having a particular property may include additional such elements not having that property.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the inventive subject matter without departing from its scope. While the dimensions and types of materials described herein are intended to define the parameters of the inventive subject matter, they are by no means limiting and are exemplary embodiments. Many other embodiments will be apparent to one of ordinary skill in the art upon reviewing the above description. The scope of the inventive subject matter should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose several embodiments of the inventive subject matter, and also to enable one of ordinary skill in the art to practice the embodiments of inventive subject matter, including making and using any devices or systems and performing any incorporated methods. The patentable scope of the inventive subject matter is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal languages of the claims.

What is claimed is:

1. A magnetic material imaging (MMI) system comprising:
   first and second sets of field-generating coils, each of the field-generating coils of the first and second sets having an elongated segment that extends along an imaging axis of the imaging system, wherein the elongated segments of the first set of field-generating coils are positioned opposite from and spaced apart from the elongated segments of the second set of field-generating coils such that a region-of-interest (ROI) of an object is configured to be located between the first and second sets of field-generating coils;
   one or more computer processors configured to control a flow of current through the first and second sets of field-generating coils to generate a selection field and to generate a drive field, the selection and drive fields combining to form a movable 1D field free region (FFR) that extends through the ROI; and
   one or more recording coils, antennas, or magnetometers positioned relative to the ROI to detect changes in magnetization of magnetic material located proximate to the 1D FFR in the ROI, wherein the drive field is a first drive field and the one or more computer processors are configured to control the flow of the current through the first and second sets of field-generating coils to generate a second drive field, each of the first and second drive fields being configured to move the 1D FFR in a different direction within the ROI, wherein the first drive field is configured to move the 1D FFR along a y-axis and the second drive field is configured to move the 1D FFR along a z-axis, the 1D FFR extending a length along an x-axis that is greater than a width of the 1D FFR along the y-axis and a height of the 1D FFR along the z-axis, the x-, y-, and z-axes being mutually perpendicular.

2. The MMI system of claim 1, wherein the one or more computer processors are configured to control the flow of the current through the first and second sets of field-generating coils to move the 1D FFR back and forth through the ROI.

3. The MMI system of claim 1, wherein the elongated segments for each of the first and second sets are positioned relative to each other to form multiple coil layers in which each coil layer includes a plurality of the elongated segments.

4. The MMI system of claim 1, further comprising an image-processing module configured to receive image data from the one or more recording coils, antennas, or magnetometers, the image data being based on measurements of the changes in magnetization.

5. The MMI system of claim 4, wherein the magnetic material is part of an instrument, the changes in magnetization within the ROI being caused by the magnetic material of the instrument, the image-processing module configured to generate a representation of the instrument within the ROI.

6. The MMI system of claim 1, further comprising a table configured to be positioned generally between the first and second sets of field-generating coils such that the object is positioned between the first and second sets of field-generating coils, the drive field extending between the first and second sets of field-generating coils.

7. The MMI system of claim 1, wherein a length for each of the elongated segments of the field-generating coils of the first and second sets is between 20 centimeters and 50 centimeters.

8. The MMI system of claim 7, wherein the 1D FFR has a cross-section transverse to a length of the 1D FFR that contains a low field region of 0.5-5.0 mm$^2$.

9. The MMI system of claim 1, wherein the 1D FFR is linear and extends parallel to the elongated segments of the first and second sets of field-generating coils.

10. The MMI system of claim 1, wherein the 1D FFR is linear and extends parallel to the elongated segments of the first and second sets of field-generating coils.

11. The MMI system of claim 1, wherein a length for each of the elongated segments of the field-generating coils of the first and second sets is between 20 centimeters and 50 centimeters.

12. A magnetic material imaging (MMI) system comprising:
first and second sets of field-generating coils, each of the field-generating coils of the first and second sets having an elongated segment that extends along an imaging axis of the imaging system, the imaging axis extending through a region-of-interest (ROI) of an object, wherein the elongated segments of the first set of field-generating coils are positioned opposite the elongated segments of the second set of field-generating coils and the ROI is located between the first and second sets of field-generating coils;
one or more computer processors configured to control a flow of current through the first and second sets of field-generating coils to generate a selection field and to generate a drive field, the selection and drive fields combining to form a movable 1D field free region (FFR) that extends through the ROI; and
one or more recording coils, antennas, or magnetometers positioned relative to the ROI to detect changes in magnetization of magnetic material located proximate to the 1D FFR in the ROI;
wherein the selection field is configured to be generated by a plurality of the elongated segments from the first set of field-generating coils and a plurality of the elongated segments from the second set of field-generating coils, and wherein the drive field is configured to be generated by a plurality of the elongated segments from the first set of field-generating coils and a plurality of the elongated segments from the second set of field-generating coils,
wherein the drive field is a first drive field and the one or more computer processors are configured to control the flow of the current through the first and second sets of field-generating coils to generate a second drive field, each of the first and second drive fields being configured to move the 1D FFR within the ROI in a space between the first and second sets of field-generating coils, wherein the first drive field is configured to move the 1D FFR along a y-axis and the second drive field is configured to move the 1D FFR along a z-axis, the 1D FFR extending a length along an x-axis that is greater than a width of the 1D FFR along the y-axis and a height of the 1D FFR along the z-axis, the x-, y-, and z-axes being mutually perpendicular.

* * * * *